(12) United States Patent
Taneja et al.

(10) Patent No.: US 7,611,845 B2
(45) Date of Patent: Nov. 3, 2009

(54) SERUM LEVELS OF HER2/NEU AS AN INDICATOR OF CLINICAL STATE AND PROGNOSIS OF PROSTATE CANCER

(75) Inventors: Samir Taneja, Wyckoff, NJ (US); Carol D. Cheli, Mahopac, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 319 days.

(21) Appl. No.: 11/312,891

(22) Filed: Dec. 19, 2005

(65) Prior Publication Data

US 2006/0160155 A1    Jul. 20, 2006

Related U.S. Application Data

(60) Provisional application No. 60/637,289, filed on Dec. 17, 2004.

(51) Int. Cl.
G01N 33/53    (2006.01)
G01N 33/574   (2006.01)

(52) U.S. Cl. .................. 435/7.1; 435/7.23

(58) Field of Classification Search ............ None
See application file for complete search history.

(56) References Cited

OTHER PUBLICATIONS

Tockman et al (Cancer Res., 1992, 52:2711s-2718s).*
Slamon et al. (Science vol. 235, Jan. 1987, pp. 177-182).*
Arai et al (The Prostate, 1997, 30:195-201, IDS).*
Shin et al (Proceedings of ASCO, 2002, 21:429a, Abstract# 1713, IDS).*
Myers et al (Int j Cancer (Pred Oncol), 1996, 69:398-402).*
Shin et al (Proceedings of ASCO, 2002, 21:429a, Abstract# 1713, IDS).*
Stein and Staros, BMC Evolutionary Biology, 2006, 6:79, p. 1-17.*
Kanamaru et al (Japanese Journal of Clinical Oncology, Mar. 1999, 29:151, internet pp. 1-9 and Figures 1, 2a, and 2b).*
Osman, I., et al., HER-2/neu (p185neu) protein expression in the natural or treated history of prostate cancer. Clin Cancer Res, 2001. 7(9): p. 2643-7.
Fossa, A., et al., Independent prognostic significance of HER-2 oncoprotein expression in pN0 prostate cancer undergoing curative radiotherapy. Int J Cancer, 2002. 99(1): p. 100-5.

Shi, Y., et al., Her-2/neu expression in prostate cancer: high level of expression associated with exposure to hormone therapy and androgen independent disease. J Urol, 2001. 166(4): p. 1514-9.
Signoretti, S., et al., Her-2-neu expression and progression toward androgen independence in human prostate cancer. J Natl Cancer Inst, 2000. 92(23): p. 1918-25.
Lara, P.N., Jr., et al., Trastuzumab plus docetaxel in HER-2/neu-positive prostate carcinoma: final results from the California Cancer Consortium Screening and Phase II Trial. Cancer, 2004. 100(10): p. 2125-31.
Scher, H.I. and G. Heller, Clinical states in prostate cancer: toward a dynamic model of disease progression. Urology, 2000. 55(3): p. 323-7.
Scher, H.I., et al., Eligibility and outcomes reporting guidelines for clinical trials for patients in the state of a rising prostate-specific antigen: recommendations from the Prostate-Specific Antigen Working Group. J Clin Oncol, 2004. 22(3): p. 537-56.
Nunes, R.A. and L.N. Harris, The HER2 extracellular domain as a prognostic and predictive factor in breast cancer. Clin Breast Cancer, 2002. 3(2): p. 125-35; discussion 136.7.
Arai, Y., T. Yoshiki, and O. Yoshida, c-erbB-2 oncoprotein: a potential biomarker of advanced prostate cancer. Prostate, 1997. 30(3): p. 195-201.
Shin, B.Y, et al, Elevated serum HER-2/neu in metastatic prostate cancer. Meeting Proceedings of the American Society of Clinical Oncology, 2002. Abstract 1713. Abstract presented at the 2002 ASCO Annual Meeting.
Ross, J.S., et al., Mol Cell Proteomics, 2004. 3.4: p. 379-398.
Morris, M.J., et al., Cancer, 2002. 94:2: p. 980-986.
Payne, R.C., et al., Clinical Chemistry, 2000, 46:2: p. 175-182.
Osman, I., et al., Serum levels of shed HER-2/neu protein in men with prostate cancer correlate with disease progression. Journal of Urology, 2005, vol. 174. p. 2174-2177.
Scher et al., "Targeting the androgen receptor: improving outcomes for castration-resistant prostate cancer," *Endocrine-Related Cancer*, 11: 459-476 (2004).
Coussens et al., "Tyrosine Kinase Receptor with Extensive Homology to EGF Receptor Shares Chromosomal Location with *neu* Oncogene," *Science*, 230: 1132-1139 (1985).

\* cited by examiner

*Primary Examiner*—Laura B Goddard
(74) *Attorney, Agent, or Firm*—Kevin Stein, Esq

(57) ABSTRACT

The present invention relates to methods of diagnosing prostate cancer, predicting disease progression of prostate cancer, prognosing the stage and state of prostate cancer, and identifying appropriate treatment indication for prostate cancer patients. Methods encompass determining the levels of HER-2/neu in fluid biological samples (e.g., blood and serum) from patients.

5 Claims, 1 Drawing Sheet

Figure 1:
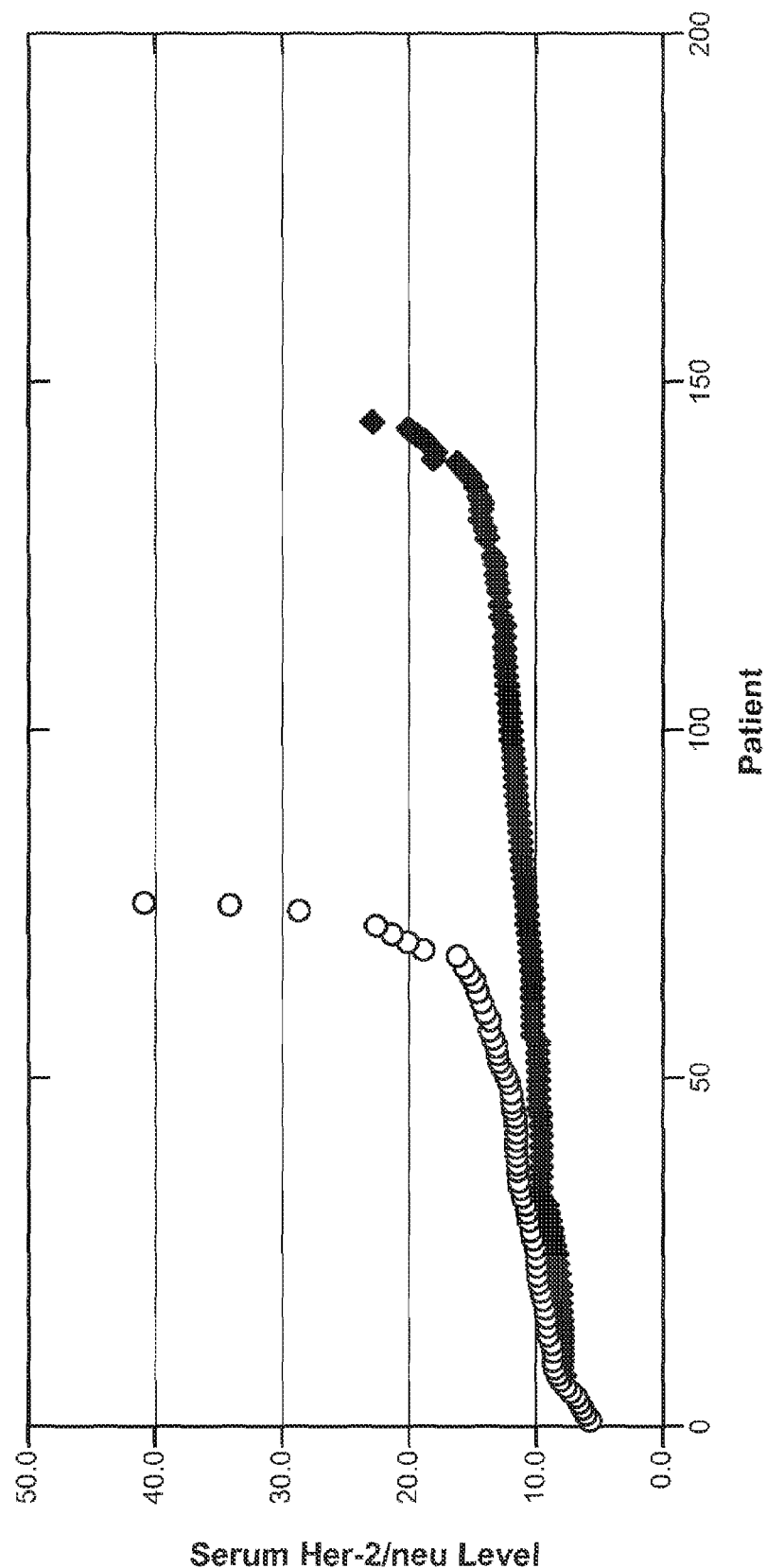

SERUM LEVELS OF HER2/NEU AS AN INDICATOR OF CLINICAL STATE AND PROGNOSIS OF PROSTATE CANCER

This application claims priority to U.S. Application Ser. No. 60/637,289 filed Dec. 17, 2004 which is incorporated by reference herein in its entirety.

1. FIELD OF THE INVENTION

The present invention relates to methods of detecting the clinical state of prostate cancer using the levels of HER-2/neu in fluid biological samples (e.g., blood and serum) from patients. Methods of identifying appropriate treatment indication for prostate cancer patients is also encompassed by the present invention.

2. BACKGROUND OF THE INVENTION

The human epidermal growth factor receptor 2/c-erbB-2 (HER-2/neu) gene is localized to chromosome 17q and it encodes a transmembrane tyrosine kinase receptor protein that is a member of the epidermal growth factor receptor family (Coussens et al., 1985, Science 230:1132). The role of Her-2/neu is best characterized in breast cancer progression, in which amplification of the Her-2/neu gene was found to correlate with tumor over expression of Her-2/neu protein and be a significant predictor of time to disease recurrence and overall survival (Ross et al., 2004, Mol Cell Proteomics 3:379). In addition, data from breast cancer clinical trials indicate that the response to anti-Her-2/neu agents was largely limited to patients with the highest Her-2/neu over expression (Cobleigh et al., 1999, J Clin Oncol. 17:2639). As a result, diagnostic tests that characterize Her-2/neu status in patients with breast cancer have been approved by the Food and Drug Administration and incorporated into the standard of care (Ross et al., 2004, Mol Cell Proteomics 3:379). Studies indicate that Her-2/neu gene amplification is a less common event in prostate cancer than it is in breast cancer (Vernimmen et al., 2003, Br J Cancer 89:899). Nevertheless, to various degrees Her-2/neu protein over expression has been demonstrated in prostate cancer tumor tissue (Shi et al., 2001, J Urol. 166:1514; Osman et al., 2001, Clin Cancer Res. 7:2643, 2001). In primary untreated disease Her-2/neu over expression is uncommon. With the administration of neoadjuvant hormone therapy expression increases significantly (Shi et al., 2001, J Urol. 166:1514; Osman et al., 2001, Clin Cancer Res. 7:2643, 2001). The highest rates of over expression observed are in tumor tissues in patients with metastatic androgen independent disease, suggesting that treatment with agents that target Her-2/neu would be most appropriate in this subset of patients. Nevertheless, no firm conclusions regarding the efficacy of the anti-Her2/neu monoclonal antibody trastuzumab in patients with metastatic androgen independent prostate cancer could be drawn in the 2 clinical trials that have been attempted (Morris et al., 2002, Cancer 94:980). Each was limited by the technical difficulties observed when sampling metastatic tissue, which is often located in bone, and in accruing an adequate number of Her-2/neu positive patients. The experience gained from these investigations highlights the need for more practical screening methods to identify patients who may be candidates for the Her-2/neu inhibitor trastuzumab as well as for the various other agents that target the Her-2/neu signaling cascade (Morris et al., 2002, Cancer 94:980). The present invention is directed to measuring Her-2/neu levels in fluid biological samples of patients with prostate cancer as a predictor of disease progression, prognosis, and treatment indications.

3. SUMMARY OF THE INVENTION

The present invention is directed to providing a minimally invasive assay for detection and prognosing prostate cancer in patients. According to the present invention, the level of human epidermal growth factor receptor 2/c-erbB-2 (HER-2/neu) is detected in a fluid biological sample (e.g., blood serum, urine, saliva, lymph, etc.) taken from a patient. Increasing levels of HER-2/neu indicate metastatic disease. Additionally, increased levels of HER-2/neu in patient body fluids can indicate that the patient is a good candidate for anti-HER-2/neu therapy.

4. BRIEF DESCRIPTION OF THE DRAWINGS

FIG. 1 is a scatterplot of Her2/neu in men with and without evaluable metastatic disease. There is a statistically significant difference in mean Her2/neu levels between men without metastatic cancer (Groups I and II, black diamonds) and men with metastatic cancer (Groups IV and V, white circles) (p0.0006).

5. DETAILED DESCRIPTION OF THE INVENTION

The contents of all published articles, books, reference manuals and abstracts cited herein, are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Modifications and variations of the present invention are possible in light of the above teachings.

6. EXAMPLES

6.1 Materials and Methods

6.1.1 Patient Characteristics

Patients were identified through review of an institutional review board approved, prospectively collected serum bank and clinical database. In this serum bank men who presented with or were suspicious for urological cancer from May 2001 to the present were enrolled, and demographic, clinical, pathological and follow up treatment data were recorded in a de-identified manner. Consenting patients had serum drawn prior to instrumentation, biopsy or digital rectal examination. Individuals with negative prostate biopsies including a minimum of 12 core samples were retained in the database and categorized as group 1 in the presented analysis. A total of 279 men consecutively enrolled in the serum bank were included for serum Her2/neu evaluation. Patients were grouped according to 5 clinical states of prostate cancer progression (Scher et al., 2000, Urology, 55:323; Scher et al:, 2004, J Clin Oncol, 22: 537) as:

Group 1 (n=60) with no evidence of cancer on prostate biopsy;

Group 2 (n=67) with clinically localized disease (T1-3, N0, M0);

Group 3 (n=77) with increasing prostate specific antigen (PSA) after any therapy and no evaluable metastases;

Group 4 (n=42) with androgen sensitive, metastatic disease; and

Group 5 (n=33) with androgen insensitive, metastatic disease.

Men in group 3 were defined by a measurable PSA of greater than 0.1 ng/ml after radical prostatectomy or 3 consecutive increasing PSA measurements at least 1 week apart, in those treated with radiation or hormonal therapy. Men in groups 4 and 5 had measurable or evaluable metastases. Each serum sample included represented a distinct patient. Serum samples used were drawn at the time of inclusion in the serum bank. As such, none of 127 men in groups 1 and 2, 38 of 77 in group 3, 29 of 42 in group 4 and all 33 in group 5 had previously been treated with hormone therapy at the time that serum was obtained.

6.1.2 Measurement of Serum Her-2/neu

Blood was centrifuged within 1 hour of collection, aliquoted immediately, frozen on dry ice and stored in a −80 C freezer. None of the samples used in this study had been thawed prior to Her2/neu assay. Samples were thawed immediately prior to assay. Measurement of HER-2/neu shed antigen levels was determined using the automated Immuno-1™ HER-2/neu assay (Bayer Diagnostics, Tarrytown, N.Y.). Immuno-1™ HER-2/neu assay technology has been previously described (Payne et al., Clin. Chem., 46:175, 2000). Briefly, the assay is a 2 site sandwich immunoassay composed of a monoclonal mouse antibody labeled with fluorescein for capture and another monoclonal antibody labeled with alkaline phosphatase for detection. These 2 monoclonal antibodies are specific for unique epitopes on the extracellular domain of HER-2/neu. Separation of bound and free detection conjugate is performed with magnetic particles coated with monoclonal antibody to fluorescein. The reaction is initiated and the measured alkaline phosphatase activity is directly proportional to the quantity of HER-2/neu antigen in the serum sample.

6.1.3 Statistical Analysis

The 95th order statistic was calculated in men in group 1 to determine the normal cutoff for Her2/neu. An exact 95% CI for the $95^{th}$ order statistic was determined by calculating 10,000 resamples of the empirical cumulative distribution of the data to determine an empirical distribution of the sample order statistic. Mean Her2/neu levels were compared between groups using the 2-sample t test and likewise a comparison of means was done between those with and without clinical metastases. Comparison of individuals in all groups was performed by 1-way ANOVA with post hoc testing for pairwise differences. Post hoc testing was done to ensure a cumulative type 1 error of no greater than 5%. Following 1-way ANOVA analysis the Levene test was performed to assess the homogeneity of variance. The Tamhane test was performed for post hoc comparisons. This test does not assume homogeneity of variance between groups. The relationship between serum Her2/neu and the risk of death in men with castrate disease (group 5) was then evaluated by a Cox proportional hazard regression model with death attributable to prostate cancer as the outcome and Her2/neu values as the covariate. All analyses were performed with SPSS for Windows™, version 11.0 (SPSS, Chicago, Ill.).

6.2 Results

The clinical characteristics of ate listed in Tables 1 and 2. Serum Her-2/neu levels in 279 men, including 60 with no evidence of cancer at initial prostate evaluation (group 1), 67 with clinically localized prostate cancer (group 2), 77 with increasing PSA after therapy (group 3), 42 with metastatic, androgen sensitive disease (group 4) and 33 with metastatic, androgen insensitive disease (group 5) were determined.

Mean Her2/neu in all patients tested was 11.5 ng/ml (range 5.2 to 40.7). The $95^{th}$ order statistic in group 1 was 13.91 ng/ml (95% CI 13.1 to 14.61). Based on this observation a conservative cutoff of 14 ng/ml was established as normal' since 95% of men with no evidence of cancer had serum Her2/neu less than 14 ng/ml.

Overall 37 of 279 patients (13.3%) had increased (greater than 14 ng/ml) serum Her-2/neu, including 3 of 60 (5%) in group 1, 8 of 67 (11.9%) in group 2, 8 of 77 (10.4%) in group 3, 7 of 42 (16.7%) in group 4 and 11 of 33 (33.3%) in group 5. Mean serum Her-2/neu generally increased with advancing disease state and 26 of 37 men (70%) with increased levels had recurrent or metastatic prostate cancer. At the time of data analysis 8 of 33 (24%) group 5 patients had died, including 7 of prostate cancer and 1 of an unrelated cause. Four of 11 patients (36%) with increased serum Her-2/neu died of prostate cancer vs 3 of 22 (13.6%) with normal serum levels.

A statistically significant difference in mean serum Her-2/neu was seen between groups 5 and 2 (p<0.02) as well as between patients with (groups 4 and 5) and without (groups 2 and 3) evaluable or measurable metastases (12.6 vs 11.0 ng/ml, p=0.006, FIG. 1). Other comparisons among individual groups and combinations of groups by 1-way ANOVA yielded no significant results (p>0.05).

Upon analysis of group 5 the risk of disease related death at any time in castrate patients with prostate cancer increased significantly by a factor of 1.1 (95% CI 1.03 to 1.20) for every 1 ng/ml increase in serum Her-2/neu (Table 3). However, the limited number of disease related deaths in our cohort precluded us from performing multivariate analysis or providing meaningful life table analysis.

6.3 Discussion

An enzyme-linked immunosorbent assay (ELISA) based assay was used to determine Her-2/neu antigen in the serum of a well characterized cohort of 279 men evaluated for prostate cancer diagnosis and treatment at the department of urology at New York University. The data revealed several important points. 1) Serum Her-2/neu shedding was uncommon in patients with prostate cancer with nonmetastatic disease. 2) Patients with metastatic disease had significantly higher mean circulating Her-2/neu protein than patients with nonmetastatic disease at presentation. 3) There was an increased risk of disease related death with increasing Her-2/neu in patients with metastatic, androgen insensitive disease. Based on these findings, serum detection of Her-2/neu offers a more practical and objective alternative to tissue sampling to determine Her-2/neu status in patients with prostate cancer who are potential candidates for Her-2/neu directed treatment strategies.

The negative prognostic impact of increased serum Her-2/neu has been demonstrated in various tumors, including breast, colorectal, pancreatic, ovarian and lung cancers (Nuneset et al., 2002, Clin Breast Cancer, 3:125, 2002; Colomer et al., 2000, Clin Cancer Res, 6: 2356; Liptonet et al., 2002, J Clin Oncol, 20: 1467; Medenet et al., 1997, Anticancer Res, 17: 757; Tsigris et al., 2002, Cancer Lett, 184:215; Ardizzoni et al, 2001, Cancer 92: 1896, 2001). In breast cancer increased serum Her-2/neu is associated with the response to trastuzumab based therapy, and resistance to chemotherapy and hormonal therapy. In colorectal cancer serum Her-2/neu has been shown to correlate with advanced disease stage and liver metastases. In ovarian cancer increased serum Her-2/neu was not associated with tumor stage or grade but it correlated significantly with decreased survival. Finally, patients with primary lung cancer who had levels higher than the 75th percentile in tumors had significantly shorter median survival than those with lower levels.

Data on the association between serum and tissue expression of Her-2/neu in prostate cancer are extremely limited. One study indicated no correlation, although this conclusion was based on only 5 patients with Her-2/neu over expression and 2 with increased serum Her-2/neu. However, another study that also showed no correlation indicated that patients who had moderate to strong Her-2/neu expression in tumor tissue were 4 times more likely to have increased serum Her-2/neu than patients with low expression. Her-2/neu tissue expression in tumors from a subset of 30 group 2 patients in whom adequate tissue was available was analyzed and found that all 3 with increased serum Her-2/neu also had increased tissue expression (data not shown). The limited number of cases with available tissue (30 of 67) as well as the low frequency of increased Her-2/neu in this group (3 of 67 or 10%) precluded any firm conclusions. Additional studies, in which a larger cohort of patients with increased serum Her-2/neu and with tumor tissues are available, are needed to better characterize this relationship in the prostate cancer setting.

Although tissue based assays can be used to determine Her-2/neu expression in various tumor types, their usefulness in prostate cancer is limited for several reasons. 1) It is extremely difficult to sample metastatic lesions located in bone. 2) The heterogeneity of Her-2/neu expression among metastatic sites may lead to false-negative assessments in patients with multiple foci of metastases. 3) Assays that rely on tissues cannot detect Her-2/neu oncoprotein shedding by residual tumor and/or circulating tumor cells. Therefore, they are inadequate for assessing the Her-2/neu status of a patient after tumor removal. In contrast, the ELISA is a blood based test that provides real-time Her-2/neu status, eliminates false-negative results due to sampling error and allows monitoring changes in Her-2/neu after treatment without the need for tissues. In our cohort 8 of 77 patients in group 3 (increasing PSA after surgery) had increased serum Her-2/neu. Despite this relatively low frequency of positive assays additional follow up in these patients will reveal whether the increased serum Her-2/neu can potentially predict recurrence.

The results demonstrated that the detection of Her-2/neu in the serum of patients with prostate cancer is a minimally invasive tool for identifying potential candidates for anti-Her-2/neu treatment strategies. Increased serum Her-2/neu has a negative impact on prognosis.

TABLE 1

| Clinical State | Patients | Age | Grade | PSA |
|---|---|---|---|---|
| 1. No cancer diagnosis | 60 | 62 | N/A | 9 |
| 2. Localized Disease | 67 | 62.9 | 6.67 | 5.4 |
| 3. Treated, PSA rising | 77 | 70.9 | 7.9 | 10 |

TABLE 1-continued

| Clinical State | Patients | Age | Grade | PSA |
|---|---|---|---|---|
| 4. Metastatic, non-castrate | 42 | 73 | 7.48 | 45 |
| 5. Metastatic, castrate | 33 | 74.9 | 7.78 | 115.8 |

TABLE 2

| | No Cancer Diagnosis 1 | Localized Prostate Cancer 2 | Treated, PSA Rising 3 | Metastatic, Non-Castrate 4 | Metastatic, Castrate 5 |
|---|---|---|---|---|---|
| Mean Serum Her-2/neu | 11.0 | 11.2 | 11.9 | 11.6 | 13.9 |
| Serum Her-2/neu Range | 7.6-16.0 | 6.1-19.8 | 7.3-23.0 | 5.2-28.9 | 6.4-40.7 |
| Serum Her-2/neu >14 ng/mL | 3/60 (5%) | 8/67 (11.9%) | 8/77 (10.4%) | 7/37 (16.7%) | 11/35 (33.3%) |

TABLE 3

Relative risk for mortality among patients with castrate, metastatic prostate cancer as a function of the deviation from mean HER-2/neu level in this group.

| HER-2/neu (ng/ml) | Mortality Relative Risk | 95% CI |
|---|---|---|
| 5 | 0.36 | 0.18-0.71 |
| 10 | 0.65 | 0.49-0.87 |
| 15 | 1.19 | 1.06-1.34 |
| 20 | 2.19 | 1.30-3.68 |
| 25 | 4.01 | 1.59-10.07 |
| 30 | 7.34 | 1.95-27.56 |
| 35 | 13.43 | 2.39-75.43 |
| 40 | 24.60 | 2.93-206.44 |

The contents of all published articles, books, reference manuals and abstracts cited herein, are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Modifications and variations of the present invention are possible in light of the above teachings.

What is claimed is:

1. A method of identifying a human patient suffering from androgen insensitive metastatic prostate cancer who has an increased risk of disease related death, comprising:
   (a) determining a level of shed human Her-2/neu protein in a blood or serum sample from the patient;
   (b) comparing said patient sample shed human Her-2/neu protein level to an average level of shed human Her-2/neu protein in comparable blood or serum samples of other human patients suffering from said cancer; and
   (c) if said patient sample shed human Her-2/neu protein level found in step(a) is increased relative to said average level of shed human Her-2/neu protein, concluding that the patient has an increased risk of disease related death relative to said other patients; and
   wherein said patient and said other patients have previously been treated with hormone therapy.

2. The method of claim 1, wherein if said patient is determined to have an increased risk of disease related death based on said increased relative level of shed human Her-2/neu protein in said sample, said patient is considered to be a candidate for anti-HER-2/neu therapy.

3. The method of claim 1, wherein the level of shed human Her-2/neu protein in the blood or serum of the patient is detected by a double antibody sandwich immunoassay comprising two monoclonal antibodies that bind different epitopes on the human Her-2/neu extracellular domain.

4. The method of claim 1, wherein said increased risk increases by a factor of 1.1 for every 1 ng/ml increase in serum human Her-2/neu protein.

5. The method of claim 1, wherein the increased level of shed human Her-2/neu protein is at least 20 ng/ml.

* * * * *

UNITED STATES PATENT AND TRADEMARK OFFICE
CERTIFICATE OF CORRECTION

PATENT NO. : 7,611,845 B2  Page 1 of 1
APPLICATION NO. : 11/312891
DATED : November 3, 2009
INVENTOR(S) : Taneja et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 560 days.

Signed and Sealed this

Fourteenth Day of December, 2010

David J. Kappos
*Director of the United States Patent and Trademark Office*